US00PP16503P2

(12) United States Plant Patent
Olesen

(10) Patent No.: US PP16,503 P2
(45) Date of Patent: May 2, 2006

(54) MINIATURE ROSE PLANT NAMED 'POULPAR033'

(50) Latin Name: ***Rosa* hybrid**
Varietal Denomination: Poulpar033

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 85 days.

(21) Appl. No.: 11/002,360

(22) Filed: Dec. 1, 2004

(51) Int. Cl.
*A01H 5/00* (2006.01)

(52) U.S. Cl. ..... Plt./116

(58) Field of Classification Search ..... Plt./116
See application file for complete search history.

*Primary Examiner*—Anne Marie Grunberg
*Assistant Examiner*—June Hwu

(57) ABSTRACT

A new miniature rose plant that has abundant, pink and white striped flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical classification: *Rosa* hybrid.
Variety denomination: 'Poulpar033'.

SUMMARY OF THE INVENTION

The present invention constitutes a new and distinct variety of miniature rose plant which originated from a controlled crossing between the female parent 'KORstoffein' described and illustrated in U.S. Plant Pat. No. 11,242 issued February 22, 2000, and the male pollen parent plant, an unnamed seedling. The two parents were crossed, and the resulting seeds were planted in a controlled environment. The new variety is named 'Poulpar033'.

The new rose may be distinguished from its seed parent, 'KORstoffein' by the following combination of characteristics:

1. 'Poulpar033' has a flower color of Red-Purple Group 67B as sepals unfold while 'KORstoffein' has a flower color of Red Group 52D with the veins, especially the mid rib, being Orange-White group 159D as sepals unfold.
2. 'Poulpar033' has a receptacle color of Yellow-Green Group 144A to 144B while 'KORstoffein' has a receptacle color of Yellow-Green Group 146C.
3. 'Poulpar033' has a petal count of 40 to 45 petals while 'KORstoffein' exhibits 25 to 30 petals.

The new variety may be distinguished from its pollen parent, created by the same inventors, by the following combination of characteristics:

1. The pollen parent achieves an overall height of 40 cm, while 'Poulpar033' is normally 20 to 30 cm in height.
2. 'Poulpar033' has small flowers between 45–55 mm while the unnamed pollen parent has larger flowers between 10 and 15 cm.

The objective of the hybridization of this rose variety for commercial culture was to create a new and distinct variety with unique qualities, such as:

1. Uniform and abundant pink and white striped flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar033' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpar033' was selected by the inventor as a single plant from the progeny of the hybridization in June 2002.

Asexual reproduction of 'Poulpar033' by cuttings and traditional budding was first done by Mogens N. Olesen in the nursery in Fredensborg, Denmark in April 2002. This initial and other subsequent propagations conducted in controlled environments have demonstrated that the characteristics of 'Poulpar033' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar033'. Specifically illustrated in the drawing:

FIG. 1.1; Flower bud closed, partially open, and open;

FIG. 1.2; Open flower;

FIG. 1.3; Sepals, receptacle, and pedicel;

FIG. 1.4; Flower petals, detached;

FIG. 1.5; Mature leaves;

FIG. 1.6; Juvenile leaves, exhibiting anthocyanin;

FIG. 1.7; Bare stem.

DETAILED DESCRIPTION OF THE VARIETY

The following is a description of 'Poulpar033', as observed in its growth in glasshouses in Odense, Denmark. Observed plants are 4 months of age, and were cultivated in 10.5 cm pots. Color references are made using The Royal Horticultural Society (London, England) Colour Chart, 2001, except where common terms of color are used.

For a comparison, several physical characteristics of the rose variety 'Poulra021', a rose variety from the same inventor, described and illustrated in U.S. Plant Pat. No. 15,506 on Feb. 1, 2005, are compared to 'Poulpar033' in Chart 1.

CHART 1

| | 'Poulpar033' | 'Poulra021' |
|---|---|---|
| Bud color as sepals unfold | Red-Purple Group 67B. | Red Group 55B. |
| Petalage. | 40 to 45. | 35 to 40. |
| Flower bloom size. | 45 to 50 mm. | 35 to 40 mm. |

FLOWER AND FLOWER BUD

Blooming habit: Continuous.

Flower bud:

*Size*.—Upon opening, 19 mm in length from base of receptacle to end of bud. 9 mm in diameter.

*Bud form*.—Ovate.

*Bud color*.—As sepals unfold, Red-Purple Group 67B.

*Sepals*.—Upper Surface: Color: Green Group 138A and 138C with Yellow-Green Group 147A at apex. Texture: Medium pubescence observed. Lower Surface: Color: Yellow-Green Group 144A and 146A. Texture: Smooth with few stipitate glands. Shape: Apex: Cirrhose. Base: Flat at union with receptacle. Margins: Margins have medium foliaceous appendages on three of the five sepals. Size: Normally, 25 to 35 mm long by 5 to 7 mm wide.

*Receptacle*.—Surface Texture: Smooth. Shape: Funnel shaped. Size: 5 mm (h)×8 mm (w). Color: Yellow-Green Group 144A to 144B.

*Peduncle*.—Surface: Somewhat rough with stipitate glands. Length: 20 to 40 mm. Diameter: 3.5 mm on average. Color: Yellow-Green Group 144B. Strength: Strong.

*Borne*.—Normally singularly. Occasionally clusters of 3 flower buds per stem observed. Inflorescence type is a corymb.

Flower bloom:

*Fragrance*.—Light floral scent.

*Duration*.—As a pot plant, flowers last up to 25 days. Petals do not fall cleanly away from plant after flowers have fully matured.

*Size*.—Flower diameter is 45 to 55 mm for a 8–11 cm pot rose. Average flower depth is 20 to 25 mm when open.

*Form*.—General shape is a rosette.

*Shape of flower when viewed from the side*.—Upon opening, upper part: Flattened convex. Upon opening, lower part: Flat. Open flower, upper part: Flattened convex. Open flower, lower part: Concave.

Petalage: Average range is 40 to 45 petals under normal conditions 5 to 10 of which are petaloids.

Petal coloration:

*Upon opening and after opening*.—Outermost petals: Upper Surface: Red-Purple Group 66C with Red-Purple 66B at the middle zone. Throughout the petal, variegation of Red-Purple 69D to White Group 155D. At the basal zone petals exhibit intonations of Yellow Group 2D. Lower Surface: Red-Purple Group 66C. Variegation the color of Red-Purple Group 69D to White Group 155D observed throughout. Innermost petals: Upper Surface: Red-Purple Group 66C to 66B. Variegation the color of Yellow Group 2B to 4C observed. Lower Surface: Red-Purple Group 66B to 66C with variegation the color of Yellow Group 4D.

*Coloration at petal base, upon opening and after opening*.—Upper Surface: Yellow Group 4B. Lower Surface: Yellow Group 4C.

General tonality: On open flower Red-Purple Group 66B to 66A. No change in the general tonality at the end of the $15^{th}$ day.

Petals:

*Petal reflex*.—Reflexed Somewhat.

*Petal margin*.—Entire and uniform.

*Shape*.—Generally broad elliptical. Base: Obtuse. Apex: Rounded.

*Size*.—Inner: 20 mm (l)×21 mm (w). Outer: 30 mm (l)×36 mm (w).

*Thickness*.—Average.

*Arrangement*.—Not formal.

*Texture*.—Smooth.

Petaloids:

*Quantity*.—Normally 5 to 10.

*Size*.—13 mm (l)×6 mm (w),

*Shape*.—Elliptical and irregular. Base: Acute. Apex: Rounded.

*Color*.—Upper Surface: Red-Purple Group 66C to 66B. Variegation the color of Yellow Group 2B to 4C observed. Lower Surface: Red-Purple Group 66B to 66C with variegation the color of Yellow Group 4D. Basal Petaloid Spots: Upper surface: Yellow Group 4B. Lower surface: Yellow Group 4C.

Reproductive organs:

*Pollen*.—None observed,

*Anthers*.—Size: 3 mm long. Color: Yellow Group 4A with margins of Yellow-Orange Group 20A, Quantity: 70.

*Filaments*.—Color: Yellow Group 5A. Length: 5 mm.

*Pistils*.—Length: 5 mm long. Quantity: Normally 45.

*Stigmas*.—Level in location relative to the length of the filaments and the height of the anthers. Color: Yellow-Green Group 144D to 144C.

*Styles*.—Color: Yellow-Green Group 144D to 144C.

*Seed formation*.—Not observed.

PLANT

Plant growth: Vigorous, compact, upright to bushy. When grown as an 8 to 11 cm potted plant on its own roots, the average height of the plant itself is 20 to 30 cm. Plant spread is normally 20 cm.

Stems:

*Color*.—Young wood: Yellow-Green Group 145A to 144B. Older wood: Yellow-Green Group 146A.

*Internodal distance*.—30 mm.

*Length of stems*.—15 cm.

*Diameter*.—2.5 mm.

*Surface texture*.—Young wood: Smooth. Older wood: Smooth.

Thorns:

*Incidence*.—3 per 10 cm of stem.

*Size*.—Average length: 3 mm.

*Color*.—Juvenile and mature thorns are Greyed-Orange Group 176A.

*Shape*.—Upper side: Flat. Lower side: Concave.

Plant foliage: Normal number of leaflets on normal leaves in middle of the stem: 5 leaflets.

*Compound leaf size*.—85 mm (l)×50 mm (w).

*Quantity*.—2 to 3 leaves per 10 cm of stem.

*Color*.—Juvenile foliage: Upper Leaf Surface: Yellow-Green Group 146A with marginal intonations of Greyed-Orange Group 176A. Lower Leaf Surface: Yellow-Green Group 147B with marginal intonations of Greyed-Orange Group 176A. Mature foliage: Upper Leaf Surface: Yellow-Green Group 147A. Lower Leaf Surface: Yellow-Green Group 147B.

Plant leaves and leaflets:

*Stipules*.—Size: 12 mm in length. Shape: Linear, slightly broad based with outward extending apecies. Margins: Finely serrated with few stipitate glands. Color: Green Group 137A.

*Petiole*.—Length: 20 mm. Diameter: 1 mm. Color: Upper surface: Yellow-Green Group 146A. Lower surface: Yellow-Green Group 145B to 144B. Observations: Few stipitate glands and light pubescence. Few small prickles observed.

*Rachis*.—Size: 25 mm. Color: Upper surface: Yellow-Green Group 146A with anthocyanin light to very intense Greyed-Red 178A. Lower surface: Yellow-Green Group 145B to 144B. Underneath: Few stipitate glands present. Few small prickles observed.

*Leaflet*.—Size: 30 to 35 mm in (l)×18×20 mm (w). Margin: Doubly serrated. General Shape: Ovate. Apex Shape: Acuminate. Base Shape: Rounded. Texture: Smooth. Thickness: Average. Arrangement: Odd pinnate. Venation: Reticulate. Leaf Gloss: Matte finish.

Disease resistance: Average resistance to powdery mildew, black spot, and *Botrytis* under normal growing conditions in Odense, Denmark.

It is claimed:

1. A new and distinct variety of rose plant of the miniature class named 'Poulpar033', substantially as illustrated and described herein, due to its abundant, pink and white striped flowers, vigorous growth, compact habit, suitability for production from softwood cuttings in pots, and durable flowers and foliage that make the variety suitable for distribution in the floral industry.

* * * * *

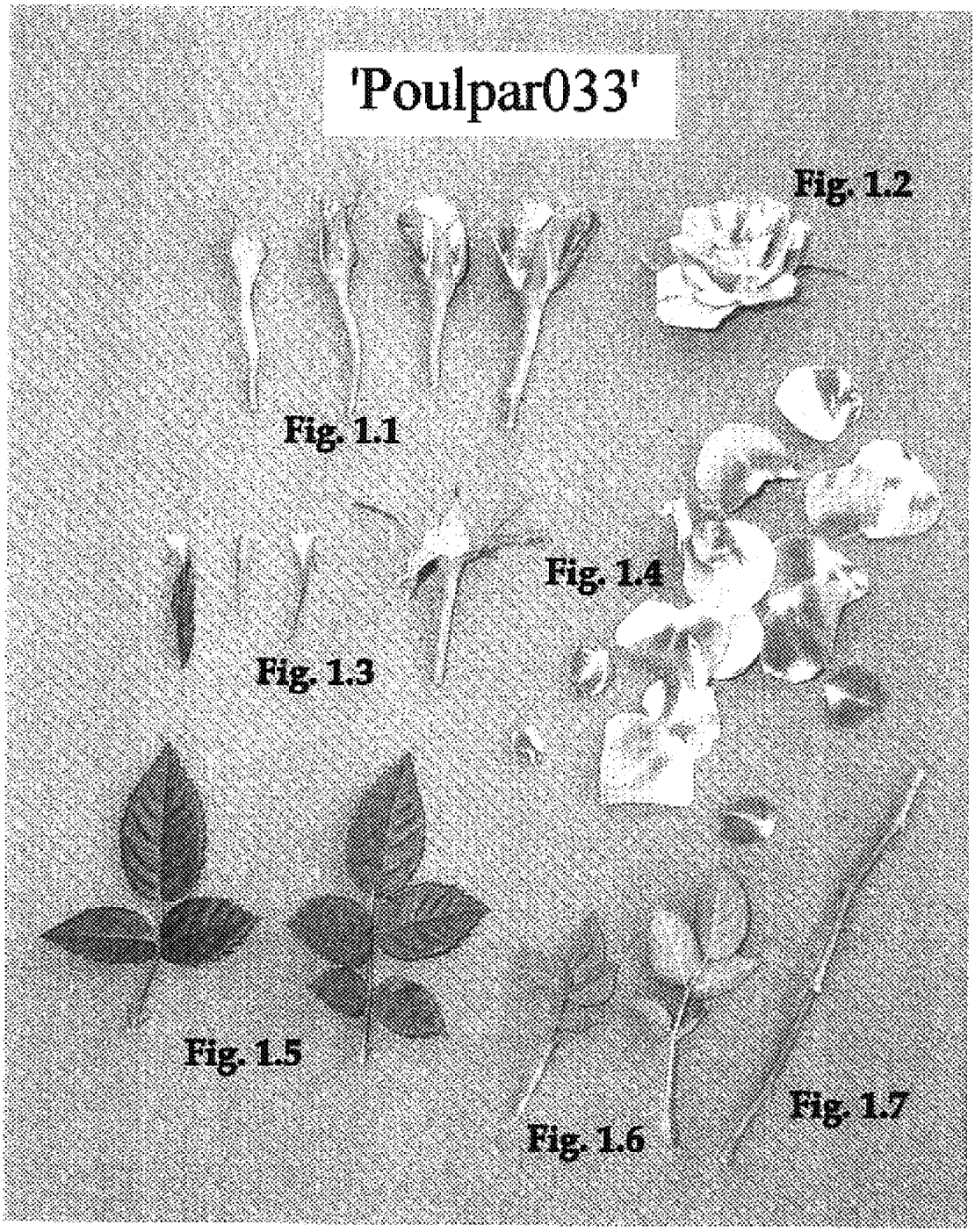
'Poulpar033'
Fig. 1.2
Fig. 1.1
Fig. 1.4
Fig. 1.3
Fig. 1.5
Fig. 1.7
Fig. 1.6